United States Patent [19]

Kalso et al.

[11] Patent Number: 5,091,402
[45] Date of Patent: Feb. 25, 1992

[54] USE OF SUBSTITUTED IMIDAZOLES

[75] Inventors: Eija Kalso, Espoo; Risto Lammintausta, Turku, both of Finland

[73] Assignee: Orion-Yhtyma OY, Espoo, Finland

[21] Appl. No.: 599,189

[22] Filed: Oct. 17, 1990

[30] Foreign Application Priority Data

Oct. 17, 1989 [FI] Finland ................................. 894911

[51] Int. Cl.⁵ .......................................... A61K 31/415
[52] U.S. Cl. .................................................. 514/396
[58] Field of Search ........................................ 514/396

Primary Examiner—Stanley J. Friedman
Attorney, Agent, or Firm—Armstrong, Nikaido, Marmelstein, Kubovcik & Murray

[57] ABSTRACT

This invention relates to local epidural or intraspinal use of compounds of the formula:

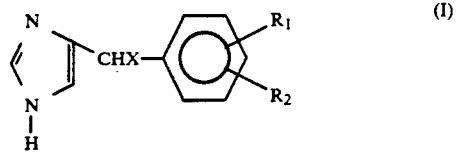

where X is H or $CH_3$ and $R_1$ and $R_2$, which can be the same or different, are each H or $CH_3$ and their stereoisomers and their non-toxic, pharmaceutically acceptable salts. Especially useful are the compounds known under the generic names medetomidine (($\pm$)-4-[1-(2,3-dimethylphenyl)ethyl]-1H-imidazole), dexmedetomidine (+)-4-[1-(2,3-dimethylphenyl)ethyl]-1H-imidazole and detomidine 4-(2,3-dimethylbenzyl)-1H-imidazole.

4 Claims, No Drawings

USE OF SUBSTITUTED IMIDAZOLES

This invention relates to local epidural or intraspinal use of compounds which are imidazoles of the

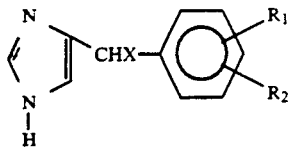

where X is H or $CH_3$ and $R_1$ and $R_2$, which can be the same or different, are each H or $CH_3$, their stereoisomers and their non-toxic, pharmaceutically acceptable salts. Especially useful are the compounds known under the generic names medetomidine (($\pm$)-4-[1-(2,3-dimethylphenyl)-ethyl]-1H-imidazole, dexmedetomidine ((+)-4-[1-(2,3-dimethylphenyl)ethyl]-1H-imidazole and detomidine (4-(2,3-dimethylbenzyl)-1H-imidazole.

Compounds of formula (I), particularly dexmedetomidine, medetomidine and detomidine are potent and selective $\alpha_2$-adrenoceptor agonists. Using systemic administration they have been shown to be potent sedative, hypotensive, and analgesic compounds and useful in anxiolytic and perioperative treatment. These compounds and uses have been described in earlier publications e.g. European Patent Publications 24829, 72615, 187471, 270267, 300652 and 331374. The usefulness of the compounds as a painkiller for chronic use is, however, limited since analgesic effects are achieved in conjunction with $\alpha_2$-adrenoceptor mediated pharmacological effects, including hypotension and sedation.

Intravenous administration of 100-300 $\mu$g/kg of the compound results in an analgesic effect, but also has a sedative and a hypotensive effect.

Intravenous administration of 1-30 $\mu$g/kg results in an anxiolytic effect but no appreciable analgesia.

The applicants have now identified a method of obtaining analgesia without producing a sedative or hypotensive effect. Such analgesia may be obtained by administering the compound intrathecally i.e. by a local epidural or intraspinal route.

Thus the present invention provides the use of a compound which is an imidazole of the formula (I):

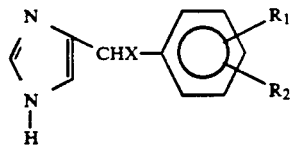

where X is H or $CH_3$ and $R_1$ and $R_2$, which can be the same or different, are each H or $CH_3$, a stereoisomer thereof or a non-toxic pharmaceutically acceptable salt thereof in the manufacture of a medicament for local epidural or intraspinal administration.

The present invention also provides a method for obtaining analgesia in a mammal comprising local epidural or intraspinal administration to the mammal of a compound which is an imidazole of the formula (I):

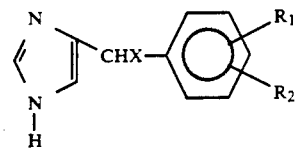

where X is H or $CH_3$ and $R_1$ and $R_2$, which can be the same or different, are H or $CH_3$, a stereoisomer thereof or a nontoxic, pharmaceutically acceptable salt thereof, in an amount effective to achieve the desired level of analgesia.

Using this method it is only necessary to administer the compound in an amount which, if administered systemically e.g. intravenously, would typically produce an anxiolytic effect. For example, dexmedetomidine administered to rats produced an almost complete antinociceptive effect at very low intrathecal doses of compound e.g. 1-30 $\mu$g/kg for rats using a standard analgesia model, the tail-flick test (ref: D'Amour F. E., Smith D. L.: A Method For Determining Loss of Pain Sensation J. Pharmacol. Exp. Ther. 1941, 72:74-79).

To achieve a similar antinociceptive effect using intravenous administration typically would require a dose of 100-300 $\mu$/kg, ten times higher than the intrathecal dose. Such intravenous analgesic doses are associated with undesirable sedative effects. On the other hand, the doses of 1-30 $\mu$g/kg, which produce analgesia at intrathecal doses, are known to have an anxiolytic, not sedative, effect when administered intravenously.

The spinal route of administration is especially useful because it avoids the side effects such a sedation and hypotension which are associated with the use of the above mentioned compounds systemically e.g. intravenously.

The present invention is illustrated by the following:

METHODS

Polyethylene catheters (8.5 cm) were inserted through the atlanto-occipital membrane with the tip at the L2 level to female Wistar rats (200-280 g) in intraperitoneal (i.p.) chloral hydrate anesthesia. After recovery for 3-5 days 400 $\mu$g of lidocaine was injected intrathecally (i.t.) and rats developing bilateral hind limb paralysis were accepted to the study. There were six rats in each group receiving either saline or dexmedetomidine in doses of 1.5, 3.0 or 6.0 $\mu$g in randomized order and double blind fashion in a volume of 10 $\mu$l. The tail-flick test (cut-off time 5 s) was performed before the i.t. injection and after 10, 20, 30, 45, 60, 90 min and 2, 3, 4, 5 and 6 h. In addition, in an open study, five rats were given atipamezole, a selective $\alpha_2$-adrenoceptor antagonist, 3 mg/kg i.p. before the injection of 6 $\mu$g of dexmedetomidine i.t.

To permit comparisons, the measured tail-flick latencies were converted to maximum percentage effect values (MPE) where MPE=100%$\times$(postinjection response latency—predrug response latency) / (cut-off time—predrug response latency). The mean maximum antinociceptive effect (91%-99%) of dexmedetomidine in doses of 3 and 6 $\mu$g was reached within 10-20 min and the MPE's differed significantly from the control group for up to 5 h. The smallest dose of 1.5 $\mu$g caused a mean maximum effect of 48%, which lasted for 45 min. The MPE's stayed below 6% in the control group.

Premedication with atipamezole abolished the antinociceptive effects of intrathecal dexmedetomidine.

The numerical data are summarized in Table 1. No signs of neurotoxicity into the spinal cord were detected.

It can be seen from this that compounds of the formula I, and in particular dexmedetomidine, causes pronounced dose dependent antinociceptive effect after doses of 1.5 to 6 µg/kg per rat or 6 to 24 µg/kg. Thus the comparison of this dose to systemic effective doses in rats and humans suggests that the effective intrathecal doses in humans would be 0.05 to 0.5 µg/kg compared to the effective systemic doses of 0.5–5 µg/kg.

These drugs could be administered to humans or other mammalian species as intrathecal or epidural injections or infusions to treat pain e.g. in surgical operations, cancer, spastic paraplegia or equivalent conditions. The injections or infusions may contain one or more diluents or carriers.

TABLE 1

Mean ± SEM values of the antinociceptive efficacy (%) at different time points after dexmedetomidine intrathecal administration.

| Time | Control (NaCl) | | | 1.5 µg DEX | | | 3 µg DEX | | | 6 µg DEX | | |
|---|---|---|---|---|---|---|---|---|---|---|---|---|
| | n | mean | SEM | n | mean | SEM | n | mean | SEM | n | mean | SEM |
| 10 min | 6 | −4.17 | 2.77 | 6 | 26.50 | 19.02 | 6 | 89.33 | 24.69 | 6 | 90.17 | 8.8 |
| 20 min | 6 | −6.67 | 2.69 | 6 | 35.00 | 18.92 | 6 | 98.67 | 1.33 | 6 | 91.00 | 9.00 |
| 30 min | 6 | −5.67 | 2.85 | 6 | 48.00 | 20.45 | 6 | 96.00 | 4.00 | 6 | 91.50 | 8.50 |
| 45 min | 6 | −5.17 | 1.69 | 6 | 45.00 | 17.98 | 6 | 95.33 | 4.67 | 6 | 91.00 | 9.00 |
| 60 min | 6 | −2.83 | 2.50 | 6 | 38.83 | 17.66 | 6 | 68.50 | 14.26 | 6 | 88.33 | 11.67 |
| 90 min | 6 | −2.83 | 2.06 | 6 | 31.83 | 17.02 | 6 | 62.50 | 18.37 | 6 | 86.00 | 9.66 |
| 2 h | 6 | −4.00 | 1.97 | 6 | 28.83 | 15.52 | 6 | 57.17 | 19.21 | 6 | 79.50 | 11.77 |
| 3 h | 6 | −2.33 | 1.82 | 6 | 12.33 | 12.07 | 6 | 53.33 | 19.01 | 6 | 76.67 | 13.72 |
| 4 h | 6 | −5.17 | 2.27 | 6 | 8.33 | 10.46 | 6 | 46.00 | 14.81 | 6 | 64.83 | 17.92 |
| 5 h | 6 | −3.17 | 1.49 | 6 | 8.50 | 7.82 | 6 | 38.33 | 13.03 | 6 | 66.50 | 13.97 |
| 6 h | 6 | −0.67 | 1.63 | 6 | 3.83 | 7.28 | 6 | 27.50 | 15.56 | 6 | 44.17 | 16.66 |
| 7 h | 3 | 3.00 | 3.00 | 5 | 10.40 | 14.30 | 6 | 33.67 | 15.95 | 5 | 34.00 | 11.48 |
| 8 h | 2 | −3.00 | 3.00 | 2 | 8.50 | 8.50 | 4 | 39.00 | 20.52 | 2 | 51.50 | 32.50 |
| 24 h | 6 | −1.67 | 1.99 | 6 | 3.33 | 4.11 | 6 | 2.33 | 1.86 | 6 | 16.67 | 13.05 |

We claim:

1. A method for obtaining analgesia in a mammal in whom analgesia without sedation is desired comprising local epidural or intraspinal administration to said mammal of a compound which is an imidazole of the formula (I):

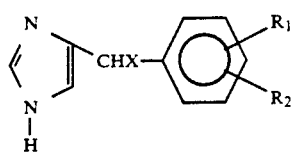

where X is H or $CH_3$ and $R_1$ and $R_2$, which can be the same or different, are H or $CH_3$, a stereoisomer thereof or a non-toxic, pharmaceutically acceptable salt thereof, in an amount effective to achieve the desired level of analgesia.

2. A method according to claim 1 in which said mammal is a human and the amount of said compound administered is an amount of said imidazole, stereoisomer or salt which corresponds to administration of 0.05 to 0.5 µg/kg of said imidazole.

3. The method according to claim 1 in which said compound is medetomidine or (±)-4-[1-(2,3-dimethylphenyl)ethyl]-1H-imidazole.

4. The method according to claim 1 in which said compound is dexmedetomidine or (±)-4-[1-(2,3-dimethylphenylethyl]-1H-imidazole.

* * * * *

UNITED STATES PATENT AND TRADEMARK OFFICE
CERTIFICATE OF CORRECTION

PATENT NO.: 5,091,402

DATED: February 25, 1992

INVENTOR(S): Eija KALSO et al.

It is certified that an error appears in the above-identified patent and that said Letters Patent is hereby corrected as shown below:

Claim 4, line 3 (col. 4, line 43), "imadizole" should read --imidazole--.

Signed and Sealed this

Eighth Day of June, 1999

Attest:

Q. TODD DICKINSON

*Attesting Officer*        *Acting Commissioner of Patents and Trademarks*

UNITED STATES PATENT AND TRADEMARK OFFICE
CERTIFICATE OF CORRECTION

PATENT NO. : 5,091,402

DATED : February 25, 1992

INVENTOR(S) : Eija Kalso, et al.

It is certified that error appears in the above-identified patent and that said Letters Patent is hereby corrected as shown below:

Claim 4, lines 2 and 3, "(±)-4-[1-(2,3-dimethylphenylethyl]-1H-imidazole" should read --(+)-4-[1-(2,3-dimethylphenyl)ethyl]-1H-imidazole--.

Signed and Sealed this

Twelfth Day of October, 1999

Q. TODD DICKINSON

Attest:

Attesting Officer

Acting Commissioner of Patents and Trademarks